(12) United States Patent
Pool

(10) Patent No.: US 11,445,939 B2
(45) Date of Patent: Sep. 20, 2022

(54) DEVICES AND METHODS FOR NON-INVASIVE IMPLANT LENGTH SENSING

(71) Applicant: NuVasive Specialized Orthopedics, Inc., San Diego, CA (US)

(72) Inventor: Scott Pool, Laguna Hills, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 232 days.

(21) Appl. No.: 16/923,733

(22) Filed: Jul. 8, 2020

(65) Prior Publication Data

US 2020/0405187 A1    Dec. 31, 2020

Related U.S. Application Data

(63) Continuation of application No. 13/253,065, filed on Oct. 4, 2011, now Pat. No. 10,743,794.

(51) Int. Cl.
| | | |
|---|---|---|
| *A61B 17/02* | (2006.01) | |
| *A61B 5/107* | (2006.01) | |
| *A61B 5/00* | (2006.01) | |
| *A61B 5/053* | (2021.01) | |

(52) U.S. Cl.
CPC .......... *A61B 5/1076* (2013.01); *A61B 5/6878* (2013.01); *A61B 17/025* (2013.01); *A61B 5/0031* (2013.01); *A61B 5/053* (2013.01)

(58) Field of Classification Search
CPC ..... A61B 5/0031; A61B 5/053; A61B 5/1076; A61B 5/6878; A61B 17/025
See application file for complete search history.

(56) References Cited

U.S. PATENT DOCUMENTS

| | | |
|---|---|---|
| 2,702,031 A | 2/1955 | Wenger |
| 3,111,945 A | 11/1963 | Von Solbrig |
| 3,372,476 A | 3/1968 | Pfeiffer |
| 3,377,576 A | 4/1968 | Langberg |

(Continued)

FOREIGN PATENT DOCUMENTS

| | | |
|---|---|---|
| CN | 1697630 A | 11/2005 |
| CN | 101040807 A | 9/2007 |

(Continued)

OTHER PUBLICATIONS

International Search Report for PCT/US2012/058499, ISA, dated Feb. 20, 2013, pp. 3.

(Continued)

*Primary Examiner* — Samuel S Hanna
(74) *Attorney, Agent, or Firm* — Hoffman Warnick LLC

(57) ABSTRACT

A device for the non-invasive sensing of the length of an implantable medical device includes an implantable medical device having first and second portions moveable relative to one another and a layer of resistive material disposed on one of the first and second portions. A contact is disposed on the other of the first and second portions, the contact being in sliding contact with the layer of resistive material upon relative movement between the first and second portions. A circuit is configured to measure the electrical resistance along a path including a variable length region of the layer of resistive material and the contact. The electrical resistance can then be converted into a length.

6 Claims, 12 Drawing Sheets

(56) References Cited

U.S. PATENT DOCUMENTS

| | | |
|---|---|---|
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,062,354 A | 12/1977 | Lyndon |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,587,850 A | 5/1986 | Moser |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |

(56) References Cited

U.S. PATENT DOCUMENTS

| | | |
|---|---|---|
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,245,117 B1 | 7/2007 | Joy et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |

(56) References Cited

U.S. PATENT DOCUMENTS

| | | |
|---|---|---|
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0097064 A1 | 5/2003 | Talpade et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138663 A1 | 7/2004 | Kosashvili et al. |
| 2004/0138725 A1 | 7/2004 | Forsell |
| 2004/0193266 A1 | 9/2004 | Meyer |
| 2005/0034705 A1 | 2/2005 | McClendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0287602 A1 | 12/2006 | O'Brien et al. |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094302 A1 | 4/2010 | Pool et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |

(56) References Cited

U.S. PATENT DOCUMENTS

| | | |
|---|---|---|
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1* | 7/2012 | Soubeiran .......... A61B 17/7216 606/86 R |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 7/2012 |
| JP | H0956736 | 3/1997 |
| JP | 2002500063 A | 1/2002 |
| WO | WO1998044858 A1 | 1/2002 |
| WO | WO1999051160 A1 | 1/2002 |
| WO | WO2001024697 A1 | 1/2002 |
| WO | WO2001045485 A3 | 1/2002 |
| WO | WO2001045487 A2 | 1/2002 |
| WO | WO2001067973 A2 | 1/2002 |
| WO | WO2001078614 A1 | 1/2002 |
| WO | 2004075727 A2 | 9/2004 |
| WO | WO2007015239 A3 | 1/2008 |
| WO | WO2007013059 A3 | 4/2009 |
| WO | WO2011116158 A3 | 1/2012 |
| WO | WO2013119528 A1 | 8/2013 |
| WO | WO2014040013 A1 | 3/2014 |

OTHER PUBLICATIONS

Abe et al., "Experimental external fixation combined with percutaneous discectomy in the management of scoliosis.", SPINE, 1999, pp. 646-653, 24, No. 7.

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Ortho fix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

(56) References Cited

OTHER PUBLICATIONS

Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.
Grass et al., "Intermittent distracting rod for correction of high neurologic risk congenital scoliosis.", SPINE, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harbach et al., "First experiences with the routine use of the Rapid Port™ system with the Lap-Band®.", Obesity Surgery, 2006, p. 418, 16, No. 4.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral mahotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering-General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?.", 39th Annual Scoliosis Research Society Meeting, 2004.

(56) References Cited

OTHER PUBLICATIONS

Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", SPINE, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791,75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.

Sun et al., "Masticatory mechanics of a mandibular distraction osteogenesis site: Interfragmentary micromovement.", Bone, 2007, pp. 188-196, 41, No. 2.
Synthes Spine, "Veptr II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 23 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", SPINE, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.

\* cited by examiner

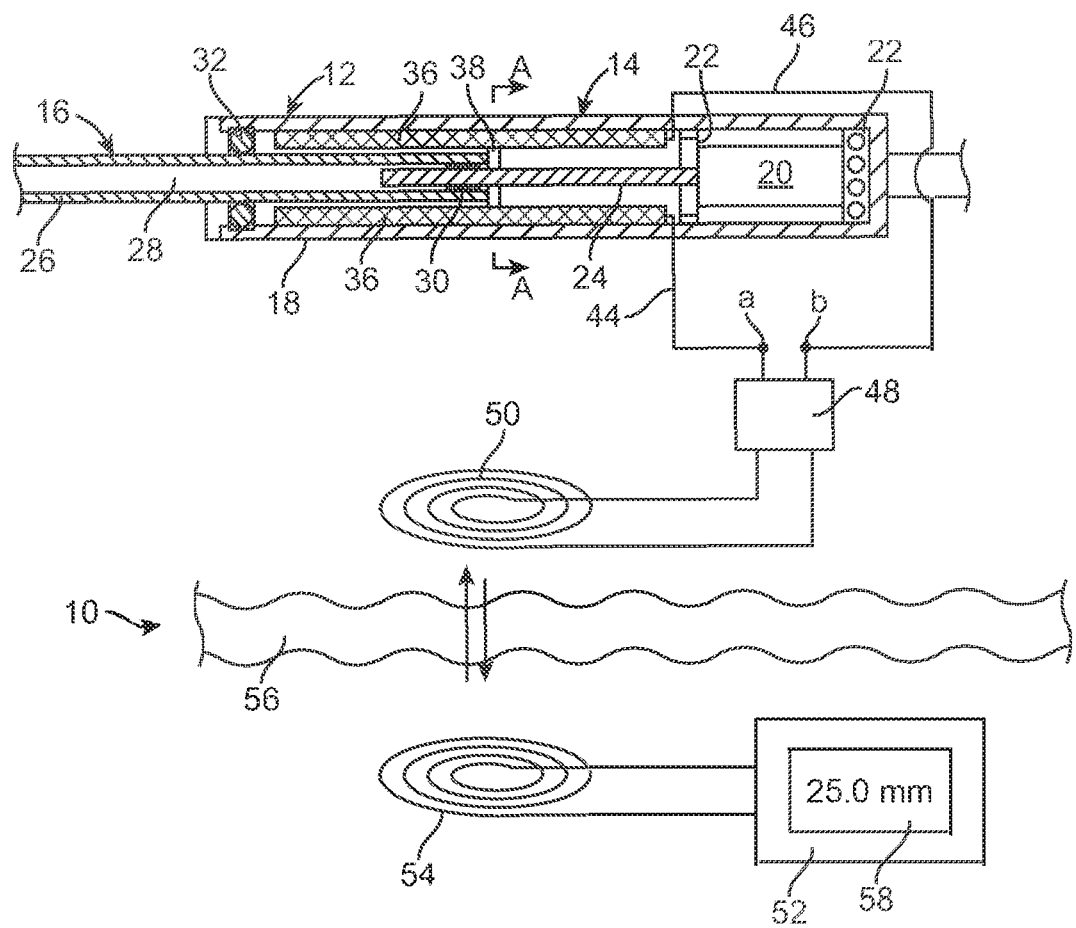
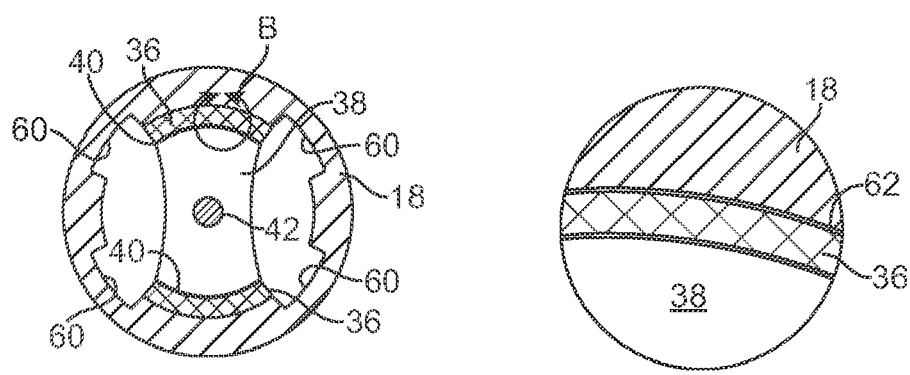
FIG. 1A
FIG. 1B
FIG. 1C

DEVICES AND METHODS FOR NON-INVASIVE IMPLANT LENGTH SENSING

FIELD OF THE INVENTION

The field of the invention generally relates to implantable medical devices and more particularly, implantable medical devices that undergo changes in length.

BACKGROUND

A variety of medical devices exist that are implanted inside the body and undergo a dimensional change. For example, a bone lengthening device is one type of implantable device that is typically inserted into first and second portions of a severed or broken bone. The device is then periodically lengthened to distract or grow the bone over a period of time. Such adjustments made to the bone lengthening device may be invasive or even non-invasive. As another example, growing rods or distraction devices may be secured to a subject's spine. These devices may be used to correct a medical condition such as scoliosis. In still other applications, these devices may be used to increase the distance between adjacent vertebrae to reduce symptoms associated with lumbar spinal stenosis or pinched nerves. Other bones such as the jaw bone may include an implantable medical device that is configured to elongate over time.

Regardless of the nature in which the implanted medical device is used, there often is a need to determine the absolute length of the implant as it exists inside the patient at any given moment. As an example, after the implanted medical device has undergone a length adjustment there is a need to determine whether or not the desired quantity of lengthening was indeed achieved. In addition, devices may change dimensions after the adjustment has been made (whether manual or non-invasive). For example, normal physiological movement of the subject may cause additional shortening or lengthening of the device after adjustment of the device. In these instances, it would be beneficial to know the actual length of the device in between adjustment procedures. For example, a physician might want to know if the device has strayed too far in either direction to warrant an additional adjustment.

U.S. Patent Application Publication No. 2010/0094302 discloses a non-invasive medical implant device that uses microphone sensor on an external adjustment device to sense when an internally-located magnet is undergoing rotation. Specifically, the microphone sensor picks up an acoustic signal (e.g., click) that is periodically generated by rotation of an internal magnet that is part of the implantable medical device. By counting the number of clicks, the external adjustment device can then translate this into an estimated length of the device. While such a method does provide a means to determine the length of the implanted medical device there is the possibility that one or more of the click signals may not be detected by the external adjustment device. In this instance, the actual length of the implanted medical device may then be different from the length that is calculated or otherwise determined by the external adjustment device. Further, while the external adjustment device may store the most current length of the device as determined by the sensed signals, it is possible that the subject may return to a different physician for his or her next adjustment procedure. Unless the size of the implanted medical device is stored locally on or with the patient (e.g., RFID or a card carried by the patient), the next physician will not know the most recent sizing of the device. Moreover, as stated above, there is the possibility that the implanted device may change lengths in between adjustment procedures. There thus is a need for methods and devices that will determine the absolute length of an implantable medical device at any given movement.

SUMMARY

In one embodiment of the invention, a device includes an implantable medical device having first and second portions moveable relative to one another and a layer of resistive material disposed on one of the first and second portions. The device includes a contact disposed on the other of the first and second portions, the contact being in sliding contact with the layer of resistive material upon relative movement between the first and second portions and a circuit configured to measure the electrical resistance along a path including a variable length region of the layer of resistive material and the contact.

In another embodiment of the invention, a method of sensing the length of an implantable medical device having first and second portions moveable relative to one another is disclosed. The implantable medical device includes a resistive pathway on one of the first and second portions of the implantable medical device along with a contact disposed on the other of the first and second portions, the contact being in sliding contact with the resistive pathway upon relative movement between the first and second portion. The electrical resistance along a path including a variable length region of the resistive pathway and the contact is measured. The measured electrical resistance is then converted to a length.

In another embodiment, a device includes an implantable medical device having first and second portions moveable relative to one another and a primary drive coil surrounding a segment of the implantable medical device containing both the first and second portions. At least one secondary coil surrounds a segment of the implantable medical device containing both the first and second portions. The device includes a first circuit configured to apply a drive voltage to the primary drive coil and measure signals in the at least one secondary coil and output a signal indicative to the length of the implantable medical device.

In another embodiment, a method of sensing the length of an implantable medical device having first and second portions moveable relative to one another includes applying a driving voltage to a primary drive coil surrounding a segment of the implantable medical device containing both the first and second portions. Signals in at least one secondary coil surrounding a segment of the implantable medical device containing both the first and second portions are measured and converted to a length.

In another embodiment, a device includes an implantable medical device having first and second portions moveable relative to one another, wherein the first and second portions are separated from one another by a dielectric material. The device includes an implantable resonant coil coupled to the first and second portions and an externally located drive coil operatively coupled to a signal generator. A frequency analyzer is operatively coupled to the drive coil configured to detect the resonant frequency of the implantable medical device, wherein said resonant frequency varies depending on the degree of relative orientation between the first and second portions.

In another embodiment a method of sensing the length of an implantable medical device having first and second portions moveable relative to one another includes providing an implantable medical device wherein the first and second portions are coupled to an implanted resonant coil. An external drive coil is driven adjacent to the implanted resonant coil with a signal generator at different frequencies. A resonant frequency of the implantable medical device is detected and the resonant frequency of the implantable medical device is converted to a length.

In another embodiment, a device includes an implantable medical device having first and second portions moveable relative to one another and an elongate member having first and second ends, the first end being secured to the first portion of the implantable medical device, the second end having secured thereto a magnet. The device includes a fulcrum on the second portion of the implantable medical device and contacts various points along the elongate member in response to relative movement of the second member relative to the first member. An externally located magnetic field source is configured to apply an oscillating magnetic field in proximity to the magnet secured to the elongate member.

In another embodiment, a method of sensing the length of an implantable medical device includes providing an implantable medical device having first and second portions moveable relative to one another, an elongate member having first and second ends, the first end being secured to the first portion of the implantable medical device, the second end having secured thereto a magnet, and a fulcrum on the second portion of the implantable medical device and in contact with various points along the elongate member in response to relative movement of the second member relative to the first member. An oscillating magnetic field is applied at different frequencies in proximity to the magnet with an externally located magnetic field source driven by a power source. The power source for the externally located magnetic field source is monitored wherein the resonant frequency of the elongate member is determined based at least in part on the current draw of the power source. The resonant frequency of the elongate member is then converted to a length.

BRIEF DESCRIPTION OF THE DRAWINGS

FIG. 1A illustrates a device that non-invasively measures the length of an implantable medical device according to one embodiment.

FIG. 1B illustrates a full sectional view of the device of FIG. 1A taken along the line A-A.

FIG. 1C illustrates view B of FIG. 1B.

DETAILED DESCRIPTION OF THE ILLUSTRATED EMBODIMENTS

Figure 1D:
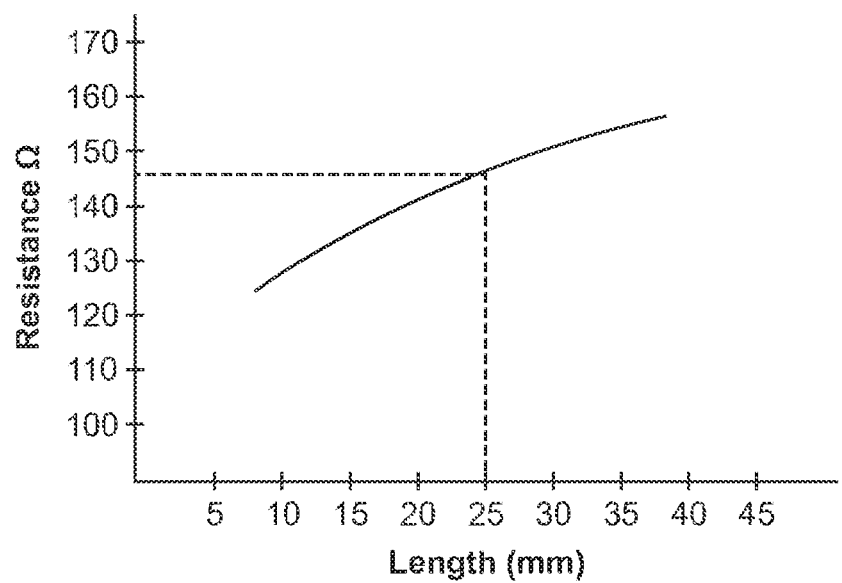
FIG. 1D illustrates a calibration curve for the device of FIGS. 1A-1C.

FIG. 1A illustrates a device 10 that non-invasively measures the length of an implantable medical device 12. The implantable medical device 12 may include any number of implantable medical devices 12 including those used to lengthen or distract bone or other tissue. These include, by way of example, distraction devices for use in bone lengthening applications (e.g., limb lengthening), spinal distraction devices for the treatment of scoliosis, spinal devices for the treatment of lumbar spinal stenosis, dental devices, and the like. The implantable medical device 12 may be one that is adjusted manually or more preferably, non-invasively. Still referring to FIG. 1A, the implantable medical device includes a first portion 14 and a second portion 16 that are moveable relative to one another. During use, the first portion 14 and second portion 16 move apart from one another for distraction or lengthening. Conversely, the first portion 14 and the second portion 16 may move toward one another for adjustment purposes or even to reduce lengthening or distraction forces. As seen in FIGS. 1A-1C, the first and second portions 14, 16 move in a telescopic fashion. In other alternative embodiments, however, the first and second portions 14, 16 do not need to be fashioned to move relative to one another in a telescopic manner. During implantation, the first portion 14 is typically secured to a first location (e.g., bone) while the second portion 16 is secured to a second, different location (e.g., different bone). Various fixation devices such as screws, pins, hooks, articulating joints, and the like may be used to secure one or both ends of the first and second portions 14, 16. In other embodiments, such as limb lengthening applications, a cavity, which may be natural or formed inside the bone, is used to receive one or both of the first and second portions 14, 16. The first and second portions 14, 16 may be secured using a mechanical fastener, cement, or method commonly known to those skilled in the art.

In the embodiment illustrated in FIGS. 1A-1C, the first portion 14 is a housing 18 in the shape of a tube or the like and is made from a biocompatible metal such as titanium. The housing 18 includes therein a permanent magnet 20 that is configured for rotational movement relative to the housing 18. The permanent magnet 20 may be formed from a rare earth magnet such as Neodymium-Iron-Boron. The permanent magnet may be made from a grade of N35 or higher, for example a grade of N50. One or more bearings 22 may be used to retain the permanent magnet 20. A lead screw 24 is connected either directly or indirectly via gears or the like (not shown) to the permanent magnet 20. Thus, rotational movement of the permanent magnet 20 causes rotational movement of the lead screw 24.

The second portion 16 of the implantable medical device 12 is in the form of a rod 26 that includes a hollow segment 28 that is dimensioned to receive the lead screw 24. A nut 30 is located within the hollow segment 28 and has threading that interfaces with threads located on the lead screw 24. Rotation of the lead screw 24 in a first direction thus causes the rod 26 to telescope into the housing 18 thus shortening the overall length of the implantable medical device 12. Conversely, rotation of the lead screw 24 in a second, opposite direction causes the rod 26 to telescope out of the housing 18 thus lengthening the overall length of the implantable medical device 12. A seal 32 is provided between the rod 26 and the housing 18 such that fluids and material remain external to the rod 26 and housing 18 during movement.

Figure 2A:
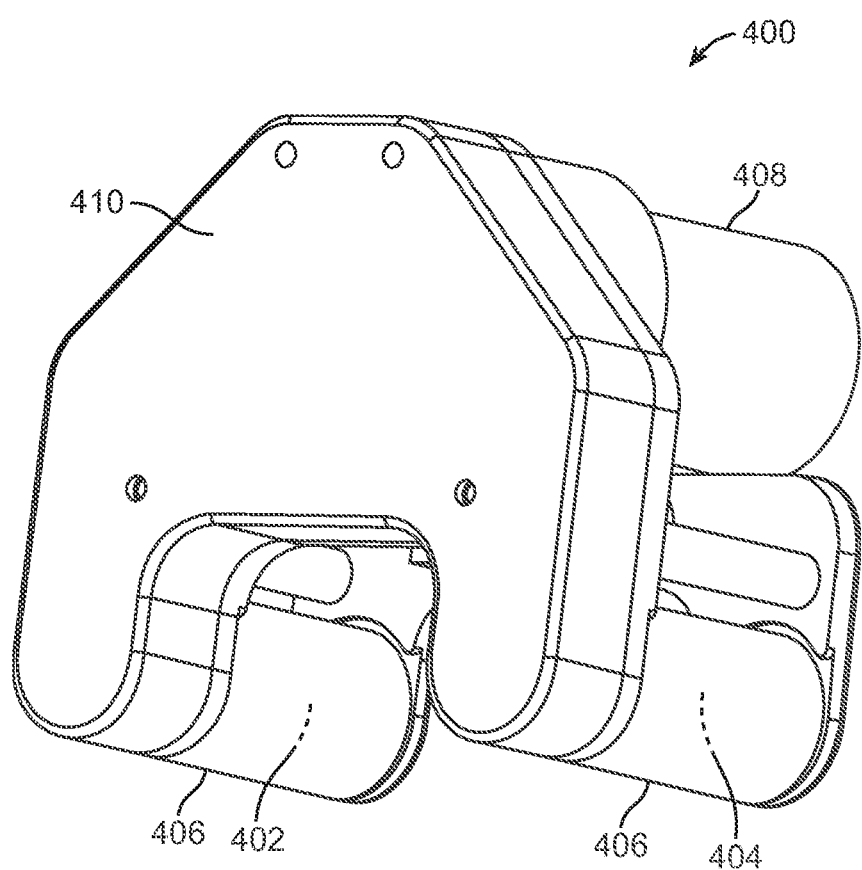
FIG. 2A illustrates a perspective view of an external adjustment device.
Figure 2B:
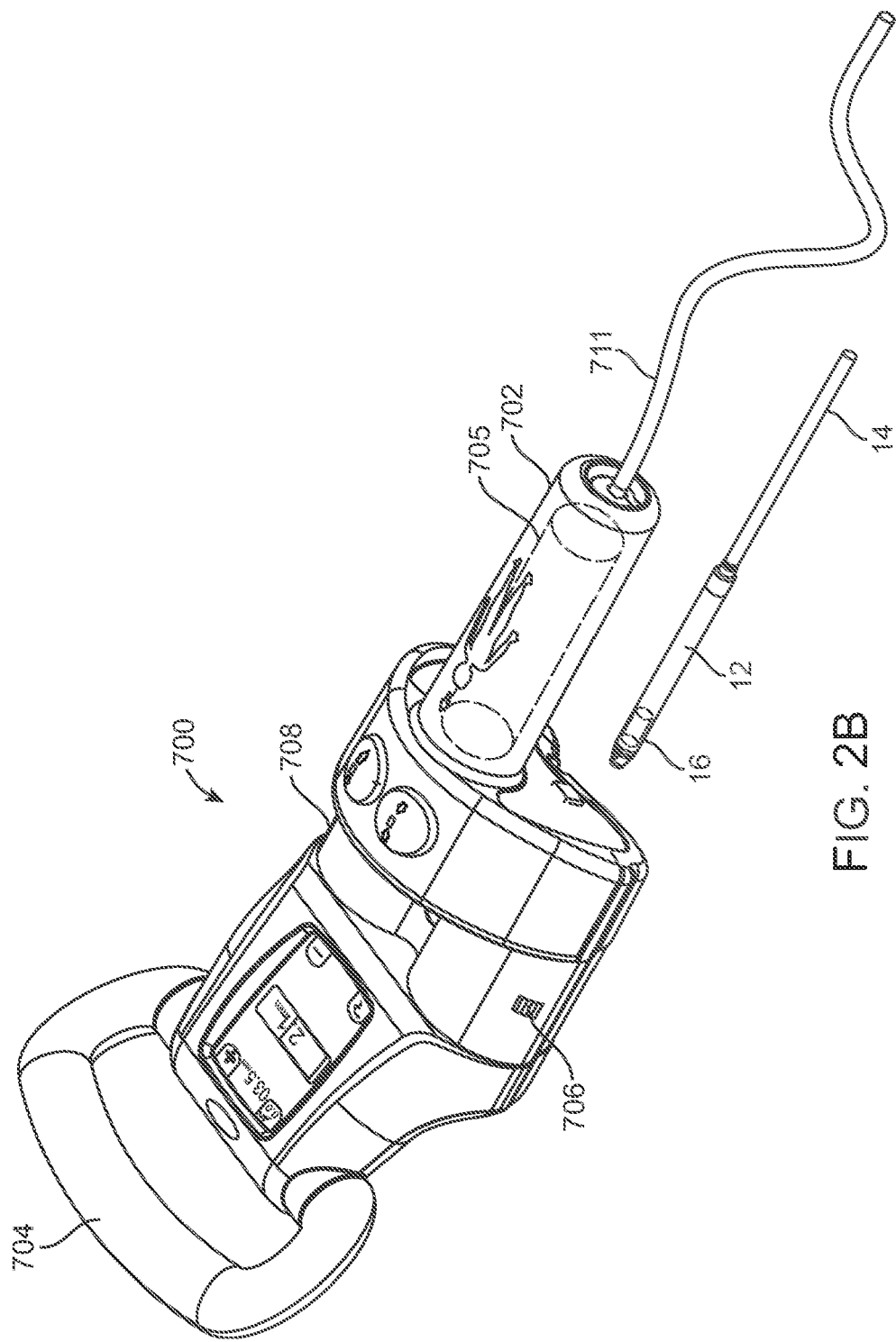
FIG. 2B illustrates a perspective view of an external adjustment device according to another embodiment.

Rotation of the permanent magnet 20 is accomplished by application of a moving magnetic field from a location external to the subject having the implantable medical device. The moving magnetic field is typically applied using an external adjustment device that has one or more rotating magnets that generate the driving magnetic field. Particular details on the nature of the external adjustment devices that can be used in connection with the distraction devices described herein are disclosed, for example, in U.S. Patent Application Publication Nos. 2009/0112207, 2010/0094302, 2010/0121323, and U.S. patent application Ser. No. 13/172, 598, all of which are incorporated by reference herein. FIG. 2A illustrates an external adjustment device 400 according to one embodiment that includes two permanent magnets 402, 404 contained within respective covers 406. Each permanent magnet 402, 404 is rotatable within its respective cover 406 and provides a moving magnetic field. A motor 408 is mechanically engaged to the permanent magnets 402, 404 via a transmission (not shown) contained within a housing 410 of the external adjustment device 400. FIG. 2B illustrates another embodiment of an external adjustment device 700. The external adjustment device includes a first handle 702 and a second handle 704. Like the prior embodiment, there are two permanent magnets 706, 708 that are rotatable and provide a moving magnetic field. A power cord 711 supplies power to a motor 705 that drives the permanent magnets 706, 708 via a gear box (not shown). Additional details regarding external adjustment device 700 may be found in U.S. application Ser. No. 13/172,598 which is incorporated by reference herein.

Referring back to FIGS. 1A-1C, the housing 18 includes a layer of resistive material 36 on an inner surface thereof. As best seen in FIGS. 1A and 1B, the housing 18 includes two separate layers of the resistive material 36 on generally opposing interior surfaces of the housing 18. It should be understood, however, that a single layer of resistive material 36 may suffice. Similarly, there may be more than two layers of resistive material 36. The layer of resistive material 36 may include any number of materials known to have a degree of electrical resistance. Exemplary materials include, for example, carbon although other known electrically resistive materials will work. Generally, in order to increase the resolution of the device 10, the resistive material 36 should have a relatively high degree of electrical resistance so that small changes in length will correspond to larger resistance differentials. An electrically conductive contact 38 is secured to the end of the rod 26. The contact 38 thus moves in conjunction with the rod 26 upon actuation of the permanent magnet 20. The contact 38 includes contact surfaces 40 that physically touch the resistive material 36. The contact surfaces 40 may include an edge, brushes, or rollers that contact the layer of resistive material 36. In this regard, the contact 38 forms part of the electrical circuit for measuring the resistance of the implantable medical device 12. Depending on the location of the rod 26, the actual length of the resistive material 36 within the electrical circuit varies. Thus, when the rod 26 is extended outward with respect to the housing 18 a larger portion of the resistive material 36 is part of the resistance circuit and resistance measurements via the circuit (discussed below in more detail) are higher. Conversely, when the rod 26 is collapsed inside the housing 18 a smaller portion of the resistive material 36 is part of the resistance circuit and resistance measurements via the circuit are lower. The contact 38 includes an aperture 42 therein for passage of the lead screw 24.

As seen in FIG. 1A, electrical conductors 44, 46 electrically connect to the two respective layers of resistive material 36. These electrical conductors 44, 46 connect to a circuit 48 which may be implemented in a microprocessor or the like. For example, the circuit 48 may include one or more processors configured to read and process measured resistance values at points a and b of the circuit in FIG. 1A. The circuit 48 may also optionally include memory for storing data therein. The memory may comprise an RFID chip. The data may include, for example, resistance values or corresponding data as well as calibration data unique to the particular implantable medical device 12. The circuit 48 is coupled to an antenna 50 which enables the circuit 48 to transmit data and other information to an externally located controller 52. The externally located controller 52 includes an antenna 54 and acts as a receiver to receive data communicated from the circuit 48. Thus, the circuit 48 acts as a transmitter while the controller 52 acts as a receiver. In one aspect of the invention, the controller 52 both powers and communicates digitally with the circuit 48. In this regard the circuit 48 does not need its own power source as the circuit 48 is powered inductively via the external controller 52. As seen in FIG. 1A, the communication occurs across the skin 56 of the subject.

The controller 52 includes a display 58 that is used to display one or more parameters indicative of the length of the implantable medical device 12. This can include a numerical value corresponding to the absolute length of the implantable medical device 12. The display 58 may also include a graphical representation of the device length (e.g., bar graph or the like) or other indicia of length. The controller 52 may also display the resistance value measured by the circuit 48.

FIG. 1B illustrates an optional feature wherein a plurality of longitudinal grooves 60 are disposed along an inner surface of the housing 18. The rod 26 includes corresponding protrusions (not shown) that form a splined tip that interfaces with the corresponding grooves 60. The tight tolerance of the splined tip with the grooves 60 keeps the rod 26 centered within the housing 18. Further, the combination of the splined tip and the grooves 60 act as an anti-rotation feature that prevents the rod 26 from rotating relative to the housing 18. Additional details regarding this optional aspect may be found in U.S. Patent Application Publication No. 2010/0217271 which is incorporated herein by reference.

FIG. 1C illustrates an enlarged view of detail B of FIG. 1B. As seen in FIG. 1C, the layer of resistive material 36 may be disposed on an insulation layer 62. The insulation layer 62 electrically insulates the layer of resistive material 36 from the underlying metallic housing 18. The insulation layer 62 may include a thin oxide layer that is formed by anodization.

To use the device 10, the external adjustment device 400 is placed near or adjacent to the patient's skin 56 near the location of implantable medical device 12. Activation of the external adjustment device 400 causes the two permanent magnets 402, 404 to rotate thereby causing the permanent magnet 20 to rotate along with the lead screw 24. Depending on the direction of rotation, the rod 26 either extends from or retracts into the housing 18. The actual length of the implantable medical device 12 is determined by measuring the resistance at points a and b using the circuit 48. The resistance measured at points a and b varies depending on the position of the contact 38 on the layer of resistive material 36. As the contact 38 moves away from the permanent magnet 20 additional resistance is added to the electrical pathway because of the additional resistive material 36 that is present in the electrical circuit. The circuit 48 measures this resistance value wherein it can be stored in the circuit 48 for later transmission or, alternatively, the resistance value may be directly transmitted to the controller 52. For example, in one aspect of the invention, when the circuit 48 is powered inductively via the external controller 52, one or more resistance measurements are made by the circuit 48 and this information is then transmitted wirelessly to the controller 52. The controller 52 can then take this data (e.g., resistance data) and convert the same to a length. For example, the controller 52 may include calibration data (calibration curve, look-up table, or the like) that is used to translate a resistance value into a length. The length can then be displayed on the display 58. The calibration data may be communicated from the circuit 48 or it may have already been pre-loaded into the controller 52. In addition, it is possible that the circuit 48 itself translates the resistance reading into a length and data corresponding to a length is transmitted to the controller 52.

FIG. 1D illustrates an illustrative calibration curve for the device of FIGS. 1A-1C. As seen in FIG. 1D, an increased resistance corresponds to an increased length of the implantable medical device 12. The calibration curve may be used for a number of different implantable medical devices 12 or it may be tailored to a single implantable medical device 12. In the example of FIG. 1D, a reading of 146 Ω corresponds to a length of 25.0 mm. Once this conversion has been made the length of 25.0 mm can then be displayed on the display 58 of the controller 52.

Figure 3A:
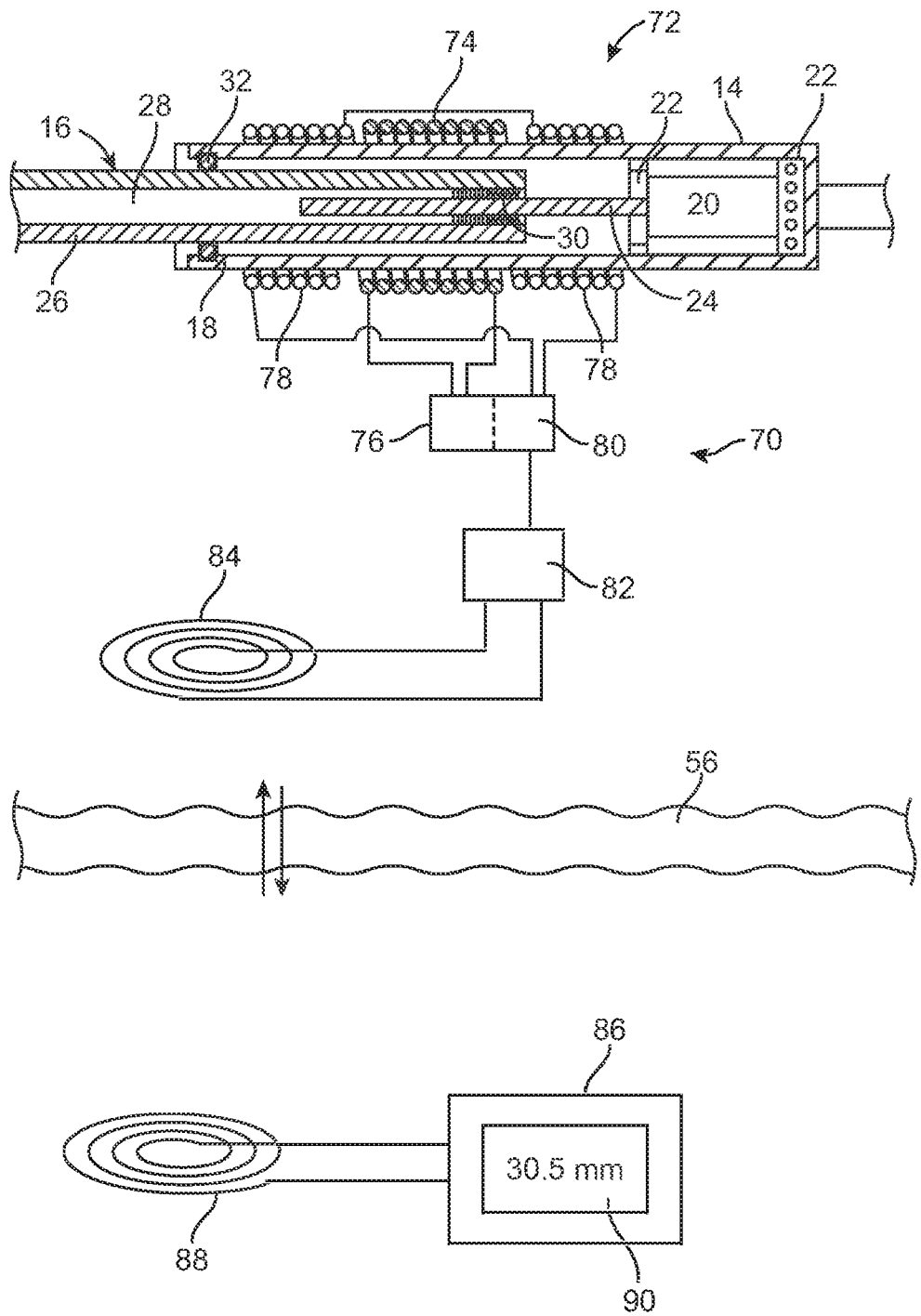
FIG. 3A illustrates a device that non-invasively measures the length of an implantable medical device according to another embodiment.

FIG. 3A illustrates an alternative embodiment of a device 70 that non-invasively measures the length of an implantable medical device 72. The implantable medical device 72 includes a first portion 14 and a second portion 16 that are moveable relative to one another. Those aspects of this embodiment of the implantable medical device 72 that are common with the embodiment of FIGS. 1A-1C are labeled with the same element numbers and will not be described again. In this embodiment, the magnetic coupling between coils is used to measure the length of the implantable medical device 72. In a similar manner to a linear variable differential transformer (LVDT) a primary coil 74 circumscribes the housing 18 and is coupled to a drive circuit 76 that delivers alternating current through the primary coil 74. A secondary coil 78 or multiple secondary coils connected in reverse series also surround the housing 18 and are coupled to a sensing circuit 80 which may be the same as or different from the drive circuit 76. The output signal from the secondary coil(s) 78, which is typically a voltage, is generally proportional to the distance moved by the rod 26 within the housing 18. The location of the primary coil 74 and the secondary coil 78 is such that the coils 74, 78 generally circumscribe the region of overlap between the rod 26 and the housing 18. By measuring the output signal with the secondary coil(s) 78, this value can then be translated into a length of the implantable medical device 72.

The sensed or decoded signal received from the secondary coil(s) 78 is then passed to a telemetry circuit 82. The telemetry circuit 82 wirelessly transmits data through the skin 56 via an antenna 84 to an external controller 86. The external controller 86 is includes an antenna 88 and acts as a receiver to receive data communicated from the telemetry circuit 82. Thus, the telemetry circuit 82 acts as a transmitter while the controller 86 acts as a receiver. In one aspect of the invention, the controller 86 both powers and communicates digitally with the telemetry circuit 82. The controller 86 may also power the sensing circuit 80. In this regard the circuits 80, 82 do not need their own power source as the circuits 80, 82 are powered inductively via the external controller 86. As seen in FIG. 3A, the communication occurs across the skin 56 of the subject.

Figure 3B:
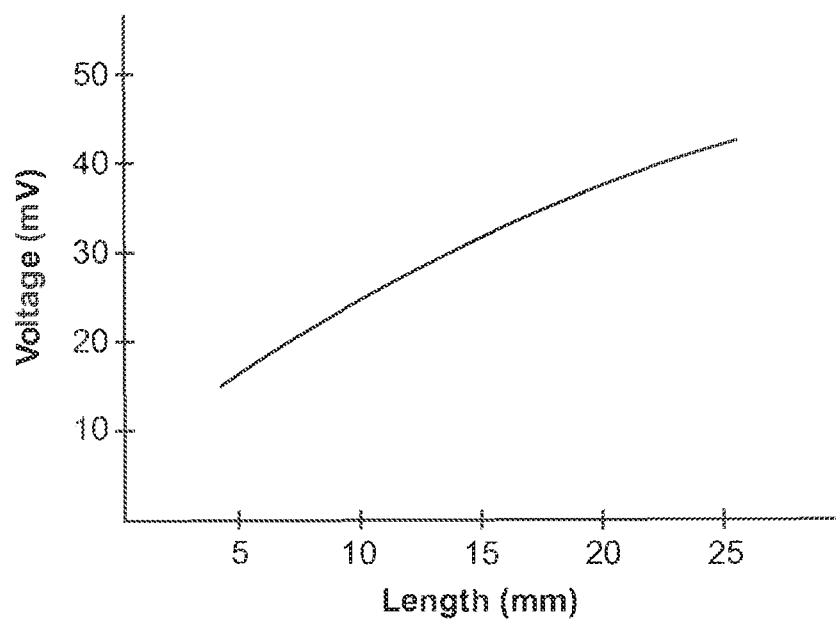
FIG. 3B illustrates a calibration curve for the device of FIG. 3A.

The controller 86, like the controller 52 of the earlier mentioned embodiment, has a display 90 that is used to display length information to a user. In one aspect of the invention, the controller 86 converts the data transmitted by the telemetry circuit 82, which may be voltage data, into length data. The controller 86 may do this by using calibration data that relates the degree of magnetic coupling (e.g., voltage output) to a length. FIG. 3B illustrates an example of a calibration that relates output (voltage) as a function of length. This calibration data may be stored in the controller 86 or transmitted from the telemetry circuit 82. Alternatively, the conversion from magnetic coupling to length can be done by the sensing circuit 80. Regardless of where the conversion is made, once a length is determined, the value can be presented to the user on the display 90.

In this embodiment, the rod 26 acts as a core that affects the degree of magnetic coupling between the primary coil 74 and the secondary coil 78. The rod 26 is preferably made from a material with a relatively high degree of magnetic permeability. This may include metals or alloys of metals. The material should also be biocompatible. Titanium and titanium alloys have excellent biocompatibility and marginal magnetic permeability. To improve on the efficiency of the resulting LVDT, a rod material with a higher magnetic permeability, such as stainless steel or other iron containing materials may be used. If a titanium or titanium alloy rod is desirable, an additional core component with higher magnetic permeability may be attached to the rod. For example a tube may be secured over the outer diameter or within an inner diameter of the rod 26. Alternatively, the nut 30 may be made from a material with higher magnetic permeability than titanium, and thus improve the effect of the core. Generally, the higher degree of magnetic permeability should translate into a device 70 with more sensitivity because an incremental movement of the rod 26 relative to the housing 18 will results in a larger change in magnetic coupling. That is to say, in the context of the calibration curve of FIG. 3B, for a given change in length, a higher degree of magnetic permeability would translate into a larger change in voltage output.

Figure 4A:
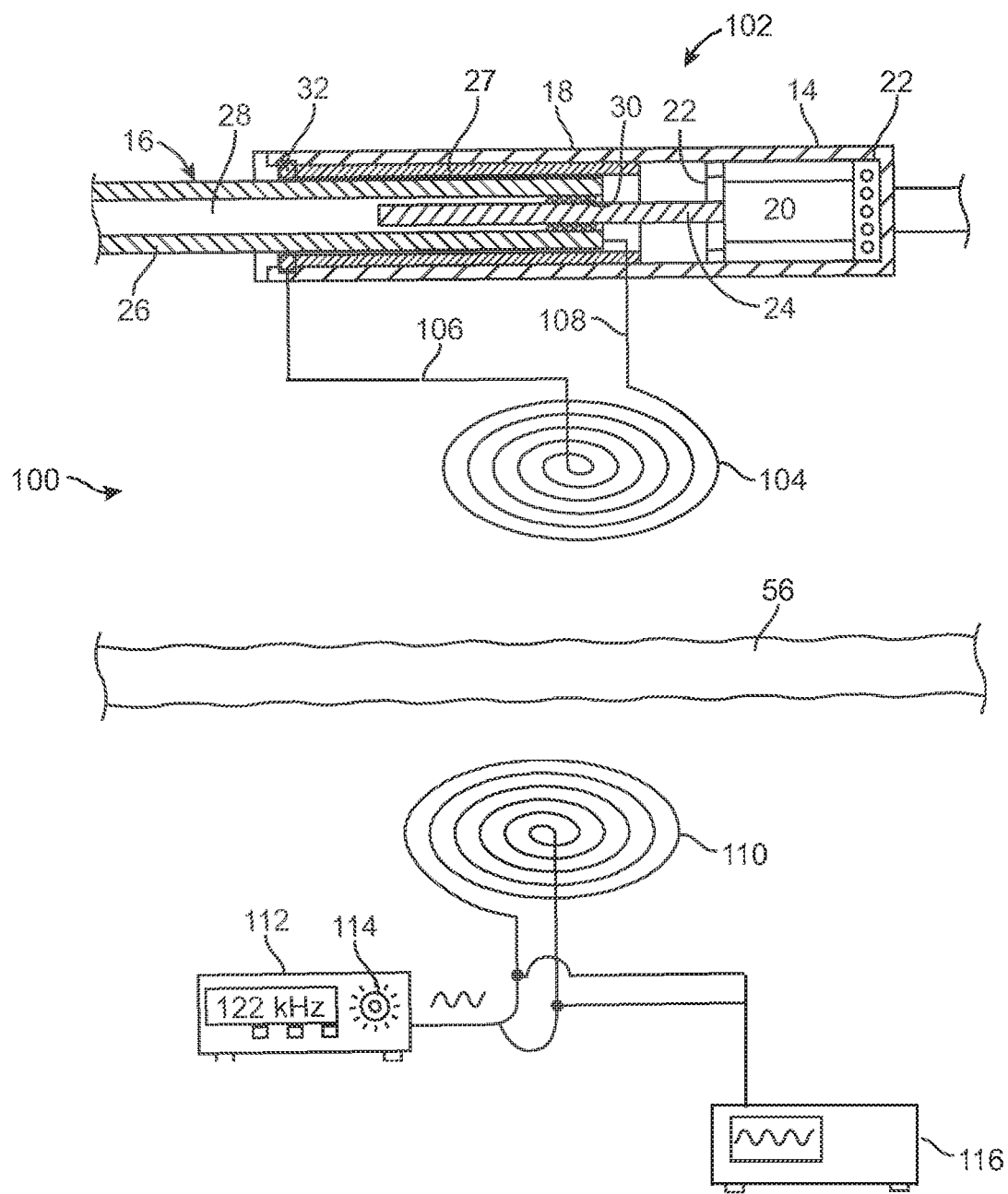
FIG. 4A illustrates a device that non-invasively measures the length of an implantable medical device according to another embodiment.

FIG. 4A illustrates another alternative embodiment of a device 100 that non-invasively measures the length of an implantable medical device 102. The implantable medical device 102 includes a first portion 14 and a second portion 16 that are moveable relative to one another. Those aspects of this embodiment of the implantable medical device 102 that are common with the embodiment of FIGS. 1A-1C are labeled with the same element numbers and will not be described again. In this device 100, a resonant coil 104 is electrically coupled to the housing 18 and the rod 26 via electrical conductors 106, 108. The electrical conductors 106, 108 may include wires, electrical traces in a printed circuit board, or the like. The rod 26 and the housing 18 are electrically isolated from one another. Electrical isolation may be accomplished by preventing the physical touching of the two components. In addition, electrical isolation may be achieved by coating one or both of the rod 26 and housing 18 with a dielectric material. This will isolate the rod 26 from the housing 18 and create a variable capacitor. A dielectric layer 27 between the rod 26 and housing 18 forms a capacitor that varies as the rod 26 moves in and out of the housing 18. The movement of the rod 26 changes the surface area of overlap between the rod and the housing thus changing the capacitance as a function of implant length. When the rod is fully retracted, the capacitance is maximized. When the rod is fully extended, the capacitance is minimized. The dielectric layer 27 may consist of a thin Kapton® (polyimide) tube bonded to the inner diameter of the housing 18, although other dielectric materials may be used (e.g., a gas such as air). Thus, the dielectric layer 27 may be applied as a layer or coating on either the rod 26 or the housing 18 (or both). Alternatively, the dielectric layer 27 may be a gap between the rod 26 and the housing 18 that is filled with air. The resonant coil 104 connected to the capacitor acts as an inductor, creating a resonant LC circuit. The device 100 further includes a drive coil 110 that is coupled to a signal generator 112. The drive coil 110 and signal generator 112 are located external to the subject with the implantable medical device 102 as illustrated in FIG. 4A. The signal generator 112 generates an alternating current (AC) signal that delivered to the drive coil 110. The drive coil 110 is located near or adjacent to the skin 56 of the subject at a location that is near or adjacent to the resonant coil 104. The resonant coil 104 may be located at a location remote from implantable medical device 102 (e.g., near the surface of the skin 56). The signal generator 112 preferably has the ability to deliver AC signals to the drive coil 110 at a variety of frequencies via input 114. The device 100 further includes a frequency analyzer 116 which may take the form of an oscilloscope or the like. The frequency analyzer 116 is used to determine when the resonant frequency of the implantable medical device 102 has been reached. In particular, the frequency of the applied AC signal is adjusted via the signal generator 112 until the frequency analyzer 116 detects that the resonant frequency has been reached. The frequency range sweep by the signal generator 112 may be automated or even manual. Detection is made when the amplitude of the signal detected by the frequency analyzer 116 drops or dips significantly. This may be detected automatically by the frequency analyzer 116. The user will thus know the resonant frequency of the implantable medical device 102 which can then be converted to a length. The particular resonant frequency of the implantable medical device 102 varies as a function of the length. A calibration curve that includes the resonant frequency of the implantable medical device 102 as a function of length can then be used determine the absolute length of the implantable medical device 102. In this regard, once the user knows the resonant frequency, the corresponding length value can be determined using the calibration curve. This can be done manually or it could be automated using a processor or computer that translates the measured resonant frequency into a length value. The frequency analyzer 116 may be separate from the signal generator 112 as seen in FIG. 4A, however, in other embodiments these two components may be integrated into a single external device as seen in FIG. 4C.

Table 1 listed below illustrates data obtained generating a calibration curve of an implantable medical device 102. Data was obtained by varying the length of the implantable medical device 102 in ¼ inch increments and adjusting the frequency of the signal generator 112 until the resonant frequency was observed with the frequency analyzer 116. In the tested device, 0.0025 inch KAPTON® polyimide tape was wrapped around the rod 26 to isolate it from the housing 18 and act as a dielectric. As noted above, the resonant frequency was determined based on a dip of the amplitude of the signal measured by the frequency analyzer 116.

TABLE 1

| Distraction (inches) | Resonant Frequency (kHz) |
|---|---|
| 0 | 104.016 |
| .25 | 110.083 |
| .50 | 116.780 |
| .75 | 123.887 |
| 1.00 | 133.136 |
| 1.25 | 141.557 |
| 1.50 | 153.635 |
| 1.75 | 168.469 |
| 2.00 | 190.366 |

Figure 4B:
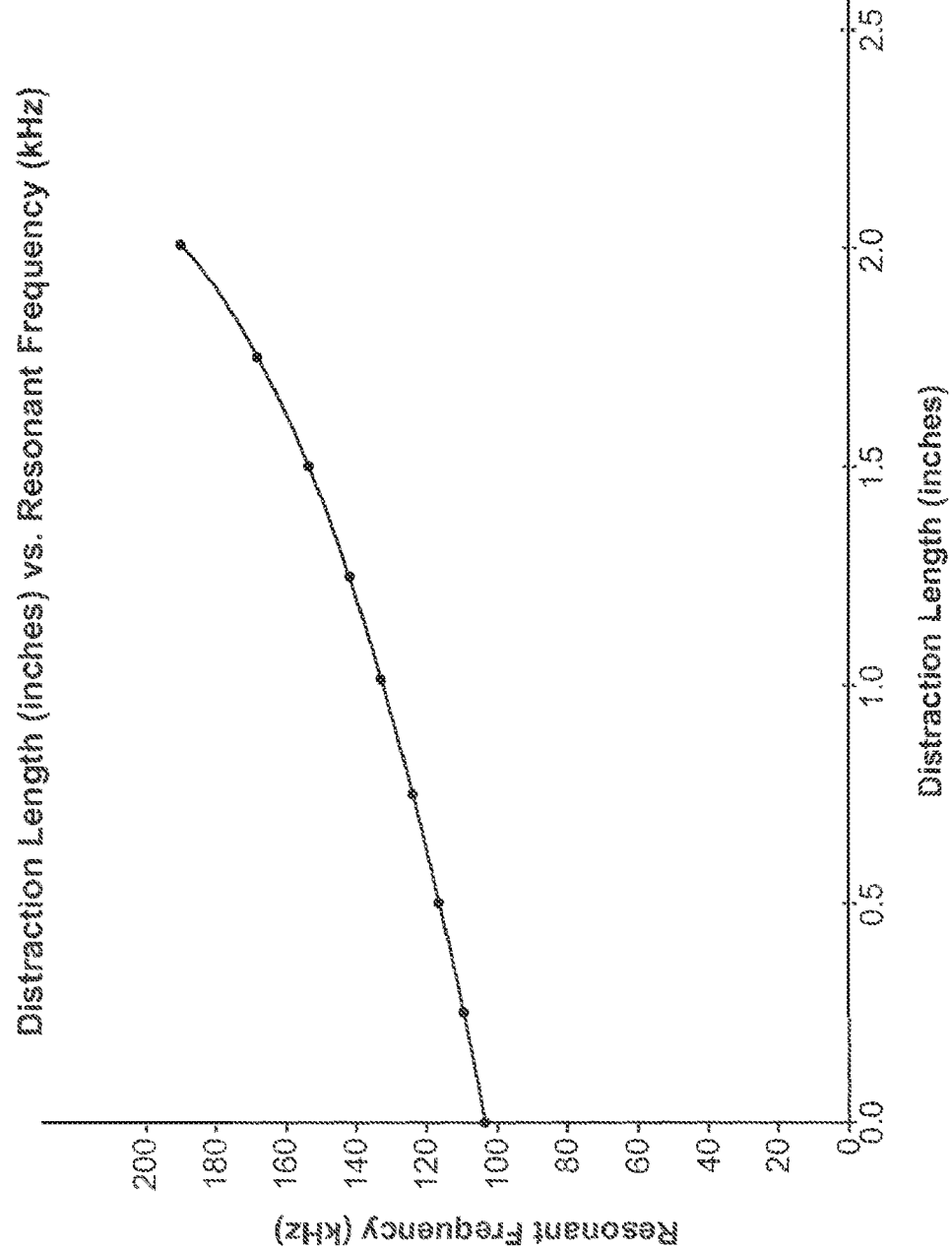
FIG. 4B illustrates a calibration curve for the device of FIG. 4A.
Figure 4C:
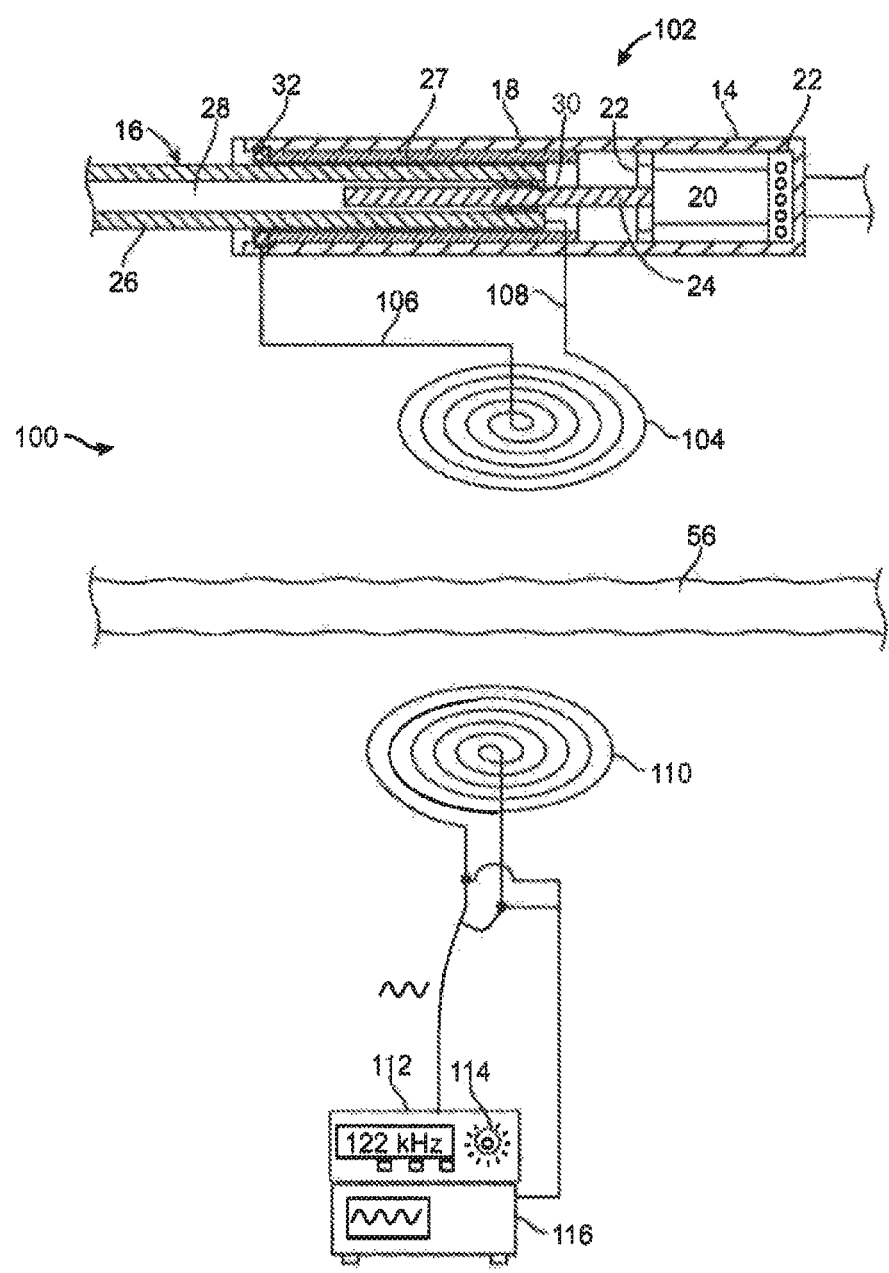
FIG. 4C illustrates another embodiment of the device of FIG. 4A.

FIG. 4B illustrates the data of Table 1 plotted as a calibration curve showing distraction length as function of resonant frequency. In this embodiment, once the resonant frequency is determined, one can then readily determine the distraction length based on the calibration curve. The calibration curve may be unique to the implantable medical device 102 and may be provided with the same or the calibration curve can be developed by the physician. Again, this method enables the physician or other skilled person to determine the absolute length of the implantable medical device 102 by non-invasive interrogation.

Figure 5A:
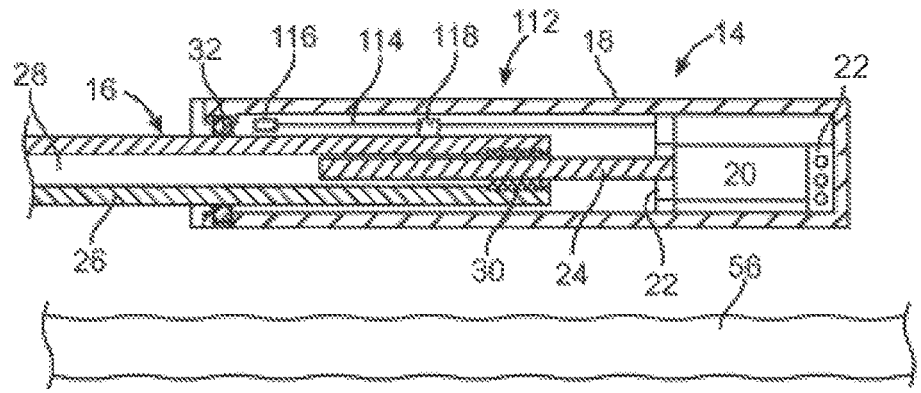
FIG. 5A illustrates a device that non-invasively measures the length of an implantable medical device according to another embodiment.
Figure 5A:
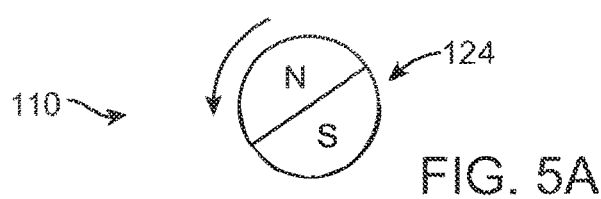
Figure 5B:
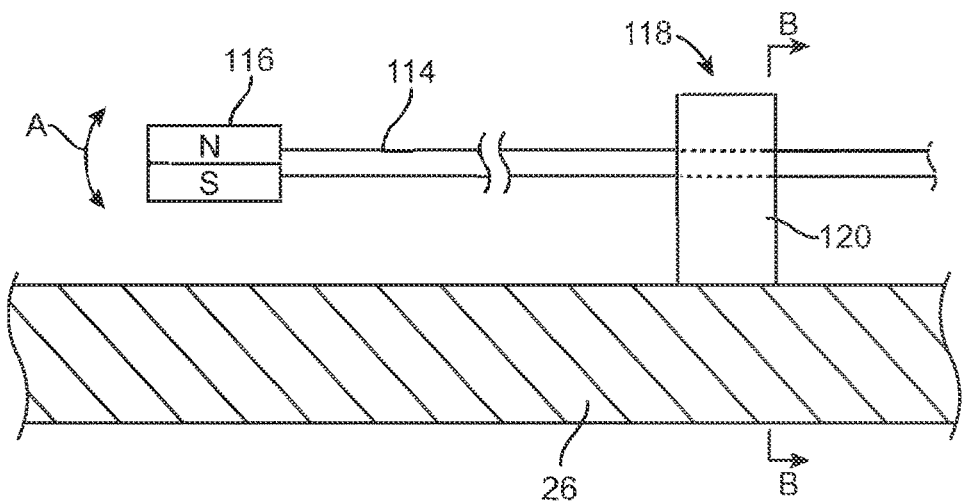
FIG. 5B illustrates an enlarged view showing the rod and fulcrum that interfaces with the elongate member having a magnet disposed on an end thereof.
Figure 5C:
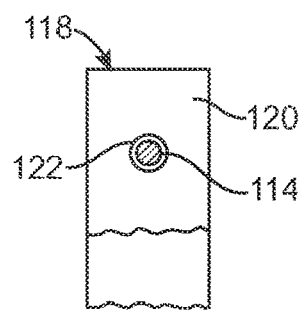
FIG. 5C illustrates a cross-sectional view taken along the line B-B of FIG. 5B.

FIGS. 5A-5E illustrate another alternative embodiment of a device 110 that non-invasively measures the length of an implantable medical device 112. The implantable medical device 112 includes a first portion 14 and a second portion 16 that are moveable relative to one another. Those aspects of this embodiment of the implantable medical device 102 that are common with the embodiment of FIGS. 1A-1C are labeled with the same element numbers and will not be described again. As best seen in FIGS. 5A and 5B, an elongate member 114 is disposed inside the housing 18 and is affixed to the housing 18 at one end thereof. On the opposing end of the elongate member 114 is located a permanent magnet 116 (best seen in FIG. 5B). The elongate member 114 passes through a fulcrum 118 that is fixedly attached to the rod 26. As best seen in FIGS. 5B and 5C, the fulcrum 118 may include a projection 120 extending from the rod 26 that includes an aperture 122 dimensioned to permit the fulcrum 118 to slide along the length of the elongate member 114 as the rod 26 is moved relative to the housing 18. In this regard, the fulcrum 118 adjusts the length of the elongate member 114 between the magnet 116 and the fulcrum 118. By changing this length, the natural vibrational frequency of the elongate member 114 changes.

Figure 5D:
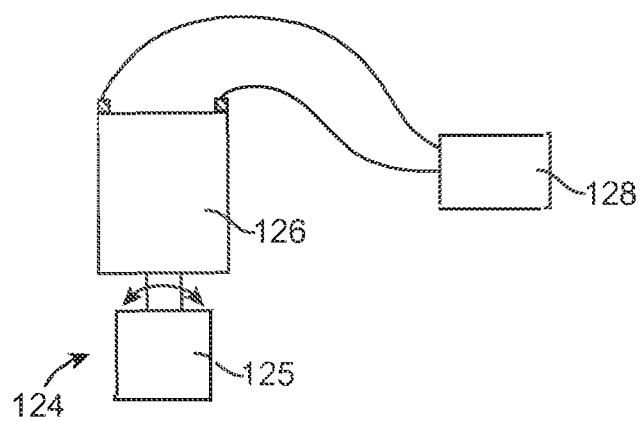
FIG. 5D illustrates a motor driven external magnet for use with the device of FIG. 5A.
Figure 5E:
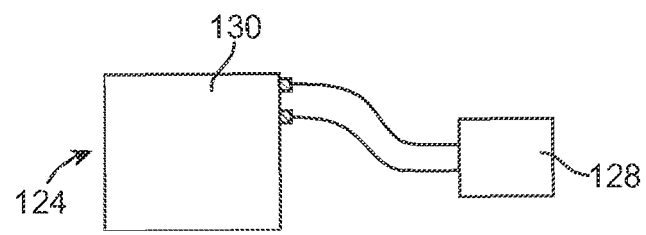
FIG. 5E illustrates an external electromagnet for use with the device of FIG. 5A.
Figure 5F:
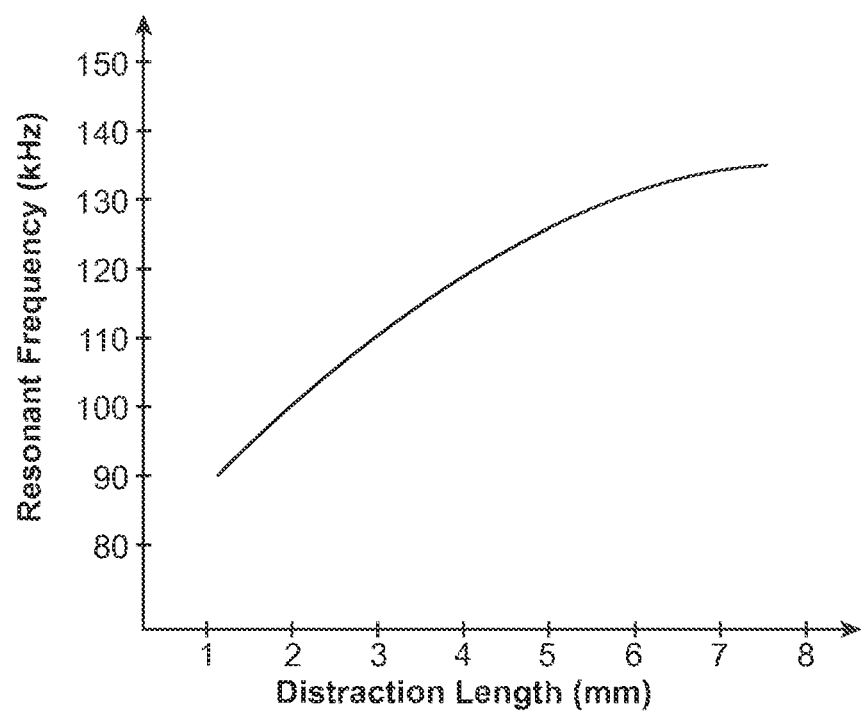
FIG. 5F illustrates a calibration curve for the device of FIG. 5A.

As part of the device 110, an externally located magnetic field source 124 is provided that applies an oscillating magnetic field to the implantable medical device 112. The oscillating magnetic field passes through the skin 56 of the subject and interacts with the magnet 116 disposed on the end of the elongate member 114. During use, the frequency of the oscillating magnetic field is adjusted (e.g., step wise adjustment) until the resonant frequency of the elongate member 114 is reached. At the resonant frequency, the magnet 116 and attached elongate member 114 vibrate back-and-forth as illustrated by arrow A of FIG. 5B. This vibration can be detected by the power that is supplied to magnetic field source 124. In one aspect, as seen in FIG. 5D, the magnetic field source 124 is a permanent magnet 125 that is rotated by a motor 126 that is powered by a driving circuit 128. The driving circuit 128 is capable of adjusting the rotational frequency of the motor 126 and thus the magnet 125. The driving circuit 128 is also able to monitor the current that drives the motor 126 using current sense circuitry. The resonant frequency is detected when a current spike is observed in the driving circuit 128. The frequency of the oscillating magnetic field can then be converted to a device length by using a calibration curve that relates length of the device to the rotational frequency of the oscillating magnetic field. FIG. 5F illustrates an exemplary calibration curve of the resonant frequency as a function of length for the device 110. The length of the device 110 may be determined by examining where the resonant frequency intersects with the calibration curve. As with all the calibration curves described herein, this may be done as a look-up table, function, or other method commonly known to those skilled in the art. As an alternative to the use of the motor 126, FIG. 5E illustrates an alternative embodiment that uses an electromagnet 130 that is driven by a driving circuit 128. Driving current can be measured by current sense circuitry in the driving circuit 128.

While embodiments have been shown and described, various modifications may be made without departing from the scope of the inventive concepts disclosed herein. For example, while the devices described in detail herein are driven non-invasively, the methods and devices are also applicable to implantable medical device that are adjusted manually. Similarly, while embodiments described in detail herein utilize a magnet coupled to a lead screw to adjust the length of an implantable medical device other drive devices may fall within the scope of the invention. Moreover, only a portion of the implantable medical device may change length or shape and be measured in a non-invasive manner. The invention(s), therefore, should not be limited, except to the following claims, and their equivalents.

What is claimed is:

1. A device comprising:
   an implantable medical device having a first portion and a second portion that are telescopically moveable relative to one another,
   wherein the first portion includes a housing having a first closed end configured to be secured to a first portion of a bone and a second open end opposite the first closed end, a first permanent magnet within the housing, and a lead screw within the housing that extends along a central axis of the housing and is rotatably secured to the first permanent magnet,
   wherein the first permanent magnet is configured to receive an oscillating magnetic field from an external source to rotate the lead screw non-invasively,
   wherein the second portion includes a rod having a first closed end configured to be secured to a second portion of the bone, a hollow segment dimensioned to receive the lead screw, and a second open end opposite to the first closed end of the rod having a threaded nut configured to engage the lead screw within the hollow segment,
   wherein the first portion is configured to telescopically move relative to the second portion by rotating the lead screw;
   an elongate member disposed within the housing of the first portion of the implantable medical device along a longitudinal axis offset from the central axis of the housing, the elongate member including a first end secured to the housing adjacent to the first permanent magnet and a second end secured to a second permanent magnet opposite the first end; and
   a fulcrum coupled to the rod of the second portion of the implantable medical device, the fulcrum including a projection that extends radially from the rod, and an aperture in the projection that is dimensioned to permit the fulcrum to slide along a length of the elongate member extending therethrough in response to relative telescopic movement of the second portion relative to the first portion.

2. The device of claim 1, further comprising:
   an externally located magnetic field source, the externally located magnetic field source configured to apply an oscillating magnetic field in proximity to the second permanent magnet secured to the elongate member.

3. The device of claim 2, wherein the externally located magnetic field source comprises an electromagnet.

4. The device of claim 3, further comprising current sense circuitry operatively coupled to the electromagnet.

5. The device of claim 2, wherein the externally located magnetic field source comprises a rotatable permanent magnet operatively connected to a motor.

6. The device of claim 5, further comprising current sense circuitry operatively coupled to the motor.

* * * * *